US008648036B2

(12) United States Patent
Wittke et al.

(10) Patent No.: US 8,648,036 B2
(45) Date of Patent: *Feb. 11, 2014

(54) USE OF NUTRITIONAL COMPOSITIONS INCLUDING LACTOFERRIN AND ONE OR MORE PREBIOTICS IN INHIBITING ADHESION OF PATHOGENS IN THE GASTROINTESTINAL TRACT

(75) Inventors: Anja Wittke, Evansville, IN (US); Dattatreya Banavara, Evansville, IN (US); Cecilia Munoz, Evansville, IN (US)

(73) Assignee: Mead Johnson Nutrition Company, Glenview, IL (US)

( * ) Notice: Subject to any disclaimer, the term of this patent is extended or adjusted under 35 U.S.C. 154(b) by 364 days.

This patent is subject to a terminal disclaimer.

(21) Appl. No.: 12/980,813

(22) Filed: Dec. 29, 2010

(65) Prior Publication Data
US 2012/0171176 A1 Jul. 5, 2012

(51) Int. Cl.
A61K 38/40 (2006.01)
A61K 31/715 (2006.01)
A01N 63/00 (2006.01)

(52) U.S. Cl.
USPC ............................ 514/2.5; 514/54; 424/93.45

(58) Field of Classification Search
USPC ................... 514/2.5, 54; 424/93.45
See application file for complete search history.

(56) References Cited

U.S. PATENT DOCUMENTS

| 4,791,193 | A | | 12/1988 | Okonogi et al. | |
|---|---|---|---|---|---|
| 4,977,137 | A | * | 12/1990 | Nichols et al. | ................. 514/5.5 |
| 5,374,567 | A | | 12/1994 | Cartagena | |
| 5,397,591 | A | | 3/1995 | Kyle et al. | |
| 5,550,156 | A | | 8/1996 | Kyle | |
| 4,849,885 | A | | 12/1998 | Nyuens et al. | |
| 5,861,491 | A | | 1/1999 | Nuijens et al. | |
| 5,919,913 | A | | 7/1999 | Nuyens et al. | |
| 7,368,141 | B2 | | 5/2008 | Lihme | |
| 7,572,474 | B2 | | 8/2009 | Petschow et al. | |
| 2004/0121042 | A1 | | 6/2004 | Kudo et al. | |
| 2006/0286258 | A1 | * | 12/2006 | Petschow et al. | ............. 426/590 |
| 2008/0003329 | A1 | | 1/2008 | Rueda et al. | |

FOREIGN PATENT DOCUMENTS

| WO | 2004026316 | 4/2004 |
|---|---|---|
| WO | 2005039319 | 5/2005 |
| WO | 2006121507 | 11/2006 |
| WO | 2008047391 | 4/2008 |
| WO | 2009068549 | 6/2009 |
| WO | 2009118771 | 10/2009 |
| WO | 2011051482 | 5/2011 |

OTHER PUBLICATIONS

Appelmelk, B., et al., "Lactoferrin is a lipid A-binding protein," Infec Immun. vol. 62, No. 6, pp. 2628-2632, Jun. 1994.
Arnold, R., et al., "Bactericidal activity of human lactoferrin: Sensitivity of a variety of microorganisms," Infec Immun. vol. 28, No. 3, pp. 893-898, Jun. 1980.
Baker, E., et al., "A structural framework for understanding the multifunctional character of lactoferrin," Biochimie. 2009;91:3-10.
Bavington, C., et al., "Stopping bacterial adhesion: a novel approach to treating infections," Respiration. 2005;72:335-344.
Caccavo, D., et al., "Antimicrobial and immunoregulatory functions of lactoferrin and its potential therapeutic application," J Endotox Res. 2002;8:403-417.
Das, N., et al., "Chemotherapy of mice experimentally infected with Shigella Ilexneri," Appl Microbiol. 1970;19:776-780.
De Araujo, A., et al., "Lactoferrin and free secretory component of human milk inhibit the adhesion of enteropathogenic *Escherichis coli* to HeLa cells," BMC Microbiology, 2001, 1:25. http://www.biomedcentral.coml1471-21S011125.
De Oliveira, I., "Binding of lactoferrin and free secretory component to enterotoxigenic *Escherichis coli*," FEMS Microbiol Lett. 2001;203:29-33.
Di Biase, A., et al., "Effect of bovine lactoferricin on Enteropathogenic Yersinia adhesion and invasion in HEp-2 cells," J Med Microbiol. 2004;53:407-412.
Di Biase, A., et al., "Heparin-interacting sites of bovine lactoferrin are involved in anti-adenovirus activity," J Med Virol. 2003;69:495-502.
Dionysius, D., et al., "Forms of' lactoferr-in: Their antibacterial effect on enterotoxigenic *Escherichia coli*," J Dairy Sci. 1993;76:2597-2606.
Dixon, D-L., et al., "Lower interleukin-S levels in airway aspirates from breastfed infants with acute bronchiolitis," Pediatr Allergy Immunol. 2010. DOI: 10.111l10j.1399-3038.2010.01011.x.
Edde, L., et al. "Lactoferrin protects neonatal rats from gut-related systemic infection," Am J Physiol Gastrointest Liver Physiol. 2001;281:G 1140-G 1150.
Ellison, R., et al., "Damage of the outer membrane of enteric gram-negative bacteria by lactoferrin and transferring," Infect Immun. 1985;56:2774-2781.
Fischer, R., et al., "Regulation of physiological and pathological Th1 and Th2 responses by lactoferrin," Biochem Cell Biol, 2006;84:303-311.
Flores-Villasenor, H., et al., "Bactericidal effect of bovine lactoferrin, LFcin, LFampin and LFchimera on antibiotic-resistant *Staphylococcus aureus* and *Escherichia coli*," BioMetals. 2010;23:569-579.
Gomez, H., et al., "Lactoferrin protects rabbits from *Shigella flexneri*-Induced inflammatory enteritis," Infec Immun. 2002;70:7050-7053.
Gomez, H., et al., "Human lactoferrin impairs virulence of *Shigella flexneri*," J Infect Dis. 2003;l87:87-95.
Gonzalez-Chavez, S., et al., "Lactoferrin: structure, function and applications," Intl. J Antimicrob Agents. 2009; 33;301.e1-301.e8.

(Continued)

*Primary Examiner* — Rosanne Kosson
(74) *Attorney, Agent, or Firm* — Waddey & Patterson, P.C.; James R. Cartiglia; Rebecca M. Barnett

(57) ABSTRACT

A method for inhibiting the adhesion of at least one pathogen in the gastrointestinal tract of a human is disclosed herein. In certain embodiments, the method involves administering to the human a nutritional composition including a fat or lipid source, a protein source, a prebiotic composition that includes galactooligosaccharide and/or polydextrose and lactoferrin produced by a non-human source.

18 Claims, No Drawings

(56) References Cited

OTHER PUBLICATIONS

Grover, M., et al., "Effect of human milk prostaglandins and lactoferrin on respiratory syncytial virus and rotavirus," Acta Paediatr. 1997;86:315-316.
Humphries et al., "Interactions of enteropathogenic *Escherichia coli* with pediatric and adult intestinal biopsy specimens during early adherence," Infect. Immun., 77, 4463-4468 (2009).
Iizumi, Y., "The Enteropathogenic *E. coli* effector EspB facilitates microvillus effacing and Antiphagocytosis by Inhibiting Myosin Function" in Cell Hosts and Microbe, pp. 383-392 (2007).
Kawasaki, Y., et al., "Inhibitory effects of bovine lactoferrin on the adherence of Enterotoxigenic *Escherichia coli* to host cells," Biosci Biotechnol Biochem. 2000;64:348-354.
King, Jr. J., et al., "A double-blind, placebo-controlled, pilot study of bovine lactoferrin supplementation in bottle-fed infants," J Pediatr Gastroenterol Nutr. 2007;44:245-251.
Kvistgaard, A., et al., "Inhibitory effects of human and bovine milk constituents on rotavirus infections,". J Dairy Sci. 2004;87:4088-4096.
Legrand, D. et al., "Interactions of lactoferrin with cells involved in immune function," Biochem Cell Biol. 2006;84:282-290.
Legrand, D. et al., "Lactoferrin: a modulator of immune and inflammatory responses," Cell Mol Life Sci. 2005;62:2549-2559.
Ling, J. et al., "Perspectives on Interactions Between Lactoferrin and Bacteria," Biochemistry and Cell Biology, pp. 275-281 (2006).
Lonnerdal, B., "Nutritional and physiologic significance of human milk proteins," Am J Clin Nutr. 2003;77:1537S-1543S.
Mange, J.P., et al., "Adhesive properties of Enterobacter sakazakii to human epithelial and brain microvascular endothelial cells," BMC Microbiol. 2006;6:58-68.
McCann, K., et al., "The effect of bovine lactoferrin and lactoferricin B on the ability of feline Calcivirus (a norovirus surrogate) and poliovirus to infect cell cultures," J Appl Microbiol. 2003;95:1026-1033.
Meijias, A., et al., "Respiratory syncytial virus persistence evidence in the mouse model," Pediatr Infect Dis J. 2008;27:S60-S62.
Miyauchi, H., et al., "Bovine lactoferrin stimulates the phagocytic activity of human neutrophils: Identification of its active domain," Cell Immunol. 1998;187:34-37.
Mosquito, S., et al., "Effect of bovine lactoferrin in *Salmonella ser.* Typhimurium infection in mice," BioMetals. DOI 10.1007/s10534-010-9325-1, Mar. 21, 2010.
Mulder, A., et al., "Bovine lactoferrin supplementation supports immune and antioxidant status in healthy human males," Nutr Res. 2008;28:583-589.
Naidu, S., et al., Relationship between antibacterial activity and porin binding of lactoferrin in *Escherichia coli* and *Salmonella typhimurium*, Antimicrob Agents and Chemother 1993;37:240-245.
Ochoa, T., "Lactoferrin Impairs Type III Secretory System Function in Enteropathogenic *Escherichia coli*," Infection and Immunity, pp. 5149-5155 (2003).
Ochoa, T., et al., "Effect of lactoferrin on enteric pathogens," Biochime. 2009;91:30-34.
Ochoa, T., et al., "Effect of lactoferrin on Enteroaggregative *E. coli* (EAEC)," Biochem Cell Biol. 2006;84:369-376.
Ochoa, T., et al., "Lactoferrin disruption of bacterial type III secretion systems," BioMetals. 2004;17:257-260.
Ochoa, T., et al., "Impact of lactoferrin supplementation on growth and prevalence of Giardia colonization in children," Clin Infect Dis. 2008;46:1881-1883.
Perez-Cano, F., et al., "Supplementing suckling rats with whey protein concentrate modulates the immune response and ameliorates rat rotavirus-induced diarrhea," J Nutr. 2008;138:2392-2398.
Pietrantoni, A., et al., "Bovine lactoferrin inhibits adenovirus infection by interacting with viral structural polypeptides," Antimicrob Agent Chemother. 2003;47:2688-2691.
Portelli, J., et al., "Effects of compounds with antibacterial activities in human milk on respiratory syncytial virus and cytomegalovirus in vitro," J Med Microbiol. 1998;47:1015-1018.

Qiu, J., et al., Human milk lactoferrin inactivates two putative colonization factors expressed by *Haemophilus influenza*, Proc Natl Acad Sci USA. 1998;95:12641-12646.
Quintero, M., et al., "Adherence inhibition of Cronobacter sakazakii to intestinal epithelial cells by pre biotic oligosaccharides,". Cur Microbiol. 2011; DOI: 10.1007/s00284-011-9882-8. Jan. 17, 2011.
Reagan-Shaw, S., et al., "Dose translation from animal to human studies revisited," FASEB J. 2008:22:659-661.
Roine, I., et al., "Breastfeeding reduces immune activation in primary respiratory syncytial virus infection," Eur Cytokine Network. 2005;16:206-210.
Database GNPD [online] www.gnpd.com, Anonymous: "Stage 1 baby formula powder," Database accession No. 1395602, Sep. 2010.
Database GNPD [online] www.gnpd.com, Anonymous: "Infant formula milk powder (state 1)," Database accession No. 1337332, Jun. 2010.
Database GNPD [online] www.gnpd.com, Anonymous: "New birth formula," Database accession No. 1249000, Jan. 2010.
Orsi, N., "The antimicrobial activity of lactoferrin: Current status and perspectives," BioMetals 17: 189-196, 2004.
Boehm, G. et al., "Prebiotic in Infant Formulas," J. Clin Gastroenteroal, Jul. 2004, vol. 38, Supp. 2 pp. S76-S79.
Kullen, M.J. et al., "The Delivery of Probiotics and Prebiotics to Infants," Current Pharmaceutical Design, 2005, vol. 11, pp. 55-74.
Weaver, L "Improving Infant Milk Formulas: Near the End of the Trail for the Holy Grail?" Journal of Pediatric Gastroenterology and Nutrition, Mar. 2003, vol. 36, pp. 301-310.
Beddek, A., "The Lactoferrin receptor complex in gram negative bacteria," Biometals, (2010) 23:377-386.
Sang, H., et al., "Lactoferrin and surfactant protein A exhibit distinct binding specificity to F protein and differently modulate respiratory syncytial virus infection," Eur J Immunol. 2003;33:2894-2902.
Santapaola, D., et al., "Effect on bovine lactoferrin on the activation of the enteroinvasive bacterial type III secretion system," BioMetals. 17: 261-265, 2004.
Sfier, R., et al., "The mode of oral bovine lactoferrin administration influences mucosal and systemic immune responses in mice," J Nutr. 2004;134:403-409.
Sharon, N., et al., "Safe as mother's milk: carbohydrates as future anti-adhesion drugs for bacterial diseases," Glycoconjugate J. 2000; 17, 659-664.
Shin, K, et al., "Effects of orally administered bovine lactoferrin and lactoperoxidase on influenza virus infection in mice," J Med Micor (2005), 54, 717-723.
Shin, K., et al., Antibacterial activity of bovine lactoferrin and its peptides against enterohaemorrhagic *Escherihia coli* O157:H7, Lett Appl Microbiol. 1998;26:407-411.
Shoaf K., et al., "Prebiotic galactooligosaccharides to reduce adherence of Enteropathogenic *Escherichia coil* to tissue culture cells," Infect Immun. 2006;74:6920-6928.
Shoaf-Sweeney, K., et al., "Adherence, anti-adherence, and oligosaccharides: preventing pathogens from sticking to the host," Adv Food Nutr Res. 2009;55:101-161.
Spadaro, M., et al., "Lactoferrin, a major defense protein of innate immunity, is a novel maturation factor for human dendritic cells," FASEB J. 2008;22:2747-2757.
Superti, F., et al., "Involvement of bovine lactoferrin metal saturation, sialic acid and protein fragments in the inhibition of rotavirus infection," Biochim Biophys Acta. 2001;1528:107-115.
Suzuki, Y., et al., "Molecular cloning and functional expression of a human intestinal lactoferrin receptor," Biochemistry. 2001;40:15771-15779.
Suzuki, Y., et al., "The N1 domain of human lactoferrin is required for internalization by Caco-2 cells and targeting to the nucleus," Biochemistry. 2008;47:10915-10920.
Suzuki, Y., et al., "Mammalian lactoferrin receptors: structure and function," Cell Mol Life Sci. 2005;62:2560-2575.
Suzuki, Y., et al., "Baculovirus expression of mouse lactoferrin receptor and tissue distribution in the mouse," BioMetals 17:301-309, 2004.

(56) References Cited

OTHER PUBLICATIONS

Takakura, N., et al., "Influences of orally administered lactoferrin on IFN-γ and IL-10 production by intestinal intraepithelial lymphocytes and mesenteric lymph-node cells," Biochem Cell Biot. 2006;84:363-368.

Van Der Strate, B., et al., "Antiviral activities of lactoferrin," Antiviral Research. 2001;225-239.

Wakabayashi, H., et al., "Modulation of immunity-related gene expression in small intestines of mice by oral administration of lactoferrin,". Clin Vaccine Immunol. 2006;13:239-245.

Yamauchi, K, et al., "Effects of orally administered bovine lactoferrin on the immune system of healthy volunteers," In: Advances in Lactoferrin Research. 1998, vol. 443, pp. 261-265.

Yamauchi, K, et al., "Bovine lactoferrin: benefits and mechanisms of action against infections," Biochem Cell Biol. 2006;84:291-296.

Yamauchi, K, et al., "Antibacterial activity of lactoferrin and a pepsin-derived lactoferrin peptide fragment," Infec Immun. 2993;61:719-728, 1993.

Zhang, G., "Neutralization of Endotoxin in Vitro and in Vivo by a Human Lactoferrin-Derived Peptide," Infection and Immunity, vol. 67, No. 3, p. 1353-1358, Mar. 1999.

* cited by examiner

SEQUENCE LISTING

<160> NUMBER OF SEQ ID NOS: 4

<210> SEQ ID NO 1
<211> LENGTH: 4
<212> TYPE: PRT
<213> ORGANISM: Homo sapiens

<400> SEQUENCE: 1

```
Arg Arg Arg Arg
1

<210> SEQ ID NO 2
<211> LENGTH: 4
<212> TYPE: PRT
<213> ORGANISM: Homo sapiens

<400> SEQUENCE: 2

Arg Lys Val Arg
1

<210> SEQ ID NO 3
<211> LENGTH: 26
<212> TYPE: PRT
<213> ORGANISM: Bos taurus

<400> SEQUENCE: 3

Phe Lys Cys Arg Arg Trp Gln Trp Arg Met Lys Lys Leu Gly Ala Pro
1               5                  10                  15

Ser Ile Thr Cys Val Arg Arg Ala Phe Ala
            20                  25

<210> SEQ ID NO 4
<211> LENGTH: 16
<212> TYPE: PRT
<213> ORGANISM: Bos taurus

<400> SEQUENCE: 4

Ala Val Gly Glu Gln Glu Leu Arg Lys Cys Asn Gln Trp Ser Gly Leu
1               5                  10                  15
```

USE OF NUTRITIONAL COMPOSITIONS INCLUDING LACTOFERRIN AND ONE OR MORE PREBIOTICS IN INHIBITING ADHESION OF PATHOGENS IN THE GASTROINTESTINAL TRACT

BACKGROUND

1. Technical Field

This disclosure relates generally to the field of nutritional compositions, such as infant formulas, human milk fortifiers, children's dietary supplements, and the like, having lactoferrin, in particular lactoferrin produced by a non-human source. More particularly, the disclosure relates to a method of inhibiting the adhesion of at least one pathogen in a human gastrointestinal tract by administering to the human a nutritional composition including lactoferrin produced by a non-human source.

2. Background

There are currently a variety of dietary compositions for humans, especially young humans, to provide supplemental or primary nutrition at certain stages in life. Generally, commercial dietary compositions for infants seek to mimic to the extent possible the composition and associated functionality of human milk. Through a combination of proteins, some of which have physiological activity, and blended fat ingredients, dietary compositions are formulated such that they simulate human milk for use as a complete or partial substitute. Other ingredients often utilized in dietary compositions for infants may include a carbohydrate source such as lactose as well as other vitamins, minerals and elements believed to be present in human milk for the absorption by the infant.

Lactoferrin is one of the primary proteins in human milk and is considered a glycoprotein having an average molecular weight of approximately 80 kilodaltons. It is an iron binding protein having the capacity to bind two molecules of iron in a reversible fashion and can facilitate the uptake of iron within the intestines for the human. Functionally, lactoferrin regulates iron absorption and as such can bind iron-based free radicals as well as donate iron for an immunological response.

An additional role of lactoferrin is its anti-microbial activity in guarding against intestinal infections in humans generally, but especially in infants. Lactoferrin has been known to be both bacteriostatic and bactericidal in inhibiting the growth of specific bacteria while also killing microbes prior to a successful invasion of intestinal cells.

In obtaining a commercially viable dietary composition, the addition of lactoferrin has generally been limited due to predicted losses of activity during processing. For example, generally, the temperature and pH requirements in processing infant formulas and other products such as human milk fortifiers and various children's products reduce specific functions of the lactoferrin, causing lactoferrin not to be included within a final formulation. In addition, lactoferrin is often considered only for its iron binding qualities; thus, lactoferrin may generally be excluded from a formulation where such properties are thought to be diminished by processing conditions.

Further, as known in the art, human breast milk is relatively low in iron, containing about 0.3 milligrams of iron per liter of breast milk. While this quantity is low, human infants have high absorption rate, absorbing about half of the iron from the breast milk. However, when human infants are given prior art formulas with high levels of iron fortification, for example, of from about 10 mg to about 12 milligrams per liter, the infants absorb less than about 5% of the total iron. With such increased levels of iron within the prior art formulas, virtually all of the lactoferrin iron binding sites would be expected to be occupied, as lactoferrin is a known iron transport protein.

Additional complications of the prior art formulas include the inability of providing a bacteriostatic effect. This is partially due to the use of lactoferrin with blocked or damaged binding sites, as the bacteriostatic effect is at least partially related to the degree of binding to iron of the lactoferrin present within the formula.

Accordingly, it would be beneficial to provide a nutritional composition, such as an infant formula, human milk fortifier, children's dietary supplement, and the like, which contains lactoferrin, in particular, lactoferrin produced by a non-human source. Preferably, the lactoferrin included in the compositions has a bacteriostatic effect even after processing under conditions of high temperature and low pH.

BRIEF SUMMARY

Briefly, the present disclosure is directed, in an embodiment, to a method for inhibiting the adhesion of at least one pathogen in the human gastrointestinal tract. In certain embodiments, the method comprises administering:

a. up to about 7 g/100 kcal of a fat or lipid source, more preferably about 3 g/100 kcal to about 7 g/100 kcal of a fat or lipid source;

b. up to about 5 g/100 kcal of a protein source, more preferably about 1 g/100 kcal to about 5 g/100 kcal of a protein source;

c. at least about 10 mg/100 kcal of lactoferrin, more preferably from about 70 mg/100 kcal to about 220 mg/100 kcal of lactoferrin produced by a non-human source, most preferably about 90 mg/100 kcal to about 190 mg/100 kcal of lactoferrin produced by a non-human source; and d. about 0.1 g/100 kcal to about 1 g/100 kcal of a prebiotic composition comprising polydextrose and/or galactooligosaccharide. More preferably, the nutritional composition comprises about 0.3 g/100 kcal to about 0.7 g/100 kcal of a prebiotic composition which comprises a combination of polydextrose and galactooligosaccharide.

Preferably, the lactoferrin is non-human lactoferrin and/or human lactoferrin produced by a genetically modified organism. The term "organism", as used herein, refers to any contiguous living system, such as animal, plant, fungus or microorganism. In one particularly preferred embodiment, the lactoferrin used is such that an effective amount of a nutritional composition containing lactoferrin may be administered to inhibit the adhesion of at least one pathogen in the gastrointestinal tract of a human, even if, during processing, the nutritional composition has been exposed to pH and temperature fluctuations typical of certain processing conditions like pasteurization. Examples of such pathogens include Enterotoxigenic *E. coli* (ETEC), Enteropathogenic *E. coli* (EPEC), *Haemophilus influenza*, Shigatoxin producing *E. coli* (STEC), Enteroaggregative *E. coli* (EAEC), *Salmonella* ser. Typhimurium, *Shigella flexneri*, Rotavirus, Norovirus, Respiratory syncytial virus (RSV), Adenovirus, and combinations thereof.

DETAILED DESCRIPTION

In certain embodiments, the present disclosure provides a method for inhibiting the adhesion of at least one pathogen in the gastrointestinal tract of a human by administering to the human nutritional compositions that comprise a lipid or fat source, a protein source, lactoferrin produced by a non-human source, and a prebiotic composition which comprises galactooligosaccharide (GOS) and/or polydextrose (PDX).

As used herein, "lactoferrin produced by a non-human source" means lactoferrin which is produced by or obtained from a source other than human breast milk. For example, lactoferrin for use in the present disclosure includes human lactoferrin produced by a genetically modified organism as well as non-human lactoferrin. The term "non-human lactoferrin", as used herein, refers to lactoferrin having an amino acid sequence that is different from the amino acid sequence of human lactoferrin.

Lactoferrins are single chain polypeptides of about 80 kD containing 1-4 glycans, depending on the species. The 3-D structures of lactoferrin of different species are very similar, but not identical. Each lactoferrin comprises two homologous lobes, called the N- and G-lobes, referring to the N-terminal and C-terminal part of the molecule, respectively. Each lobe further consists of two sub-lobes or domains, which form a cleft where the ferric ion ($Fe^{3+}$) is tightly bound in synergistic cooperation with a (bi)carbonate anion. These domains are called N1, N2, C1 and C2, respectively. The N-terminus of lactoferrin has strong cationic peptide regions that are responsible for a number of important binding characteristics. Lactoferrin has a very high isoelectric point (~pI 9) and its cationic nature plays a major role in its ability to defend against bacterial, viral, and fungal pathogens. There are several clusters of cationic amino acids residues within the N-terminal region of lactoferrin mediating the biological activities of lactoferrin against a wide range of microorganisms. For instance, the N-terminal residues 1-47 of human lactoferrin (1-48 of bovine lactoferrin) are critical to the iron-independent biological activities of lactoferrin. In human lactoferrin, residues 2 to 5 (RRRR) (i.e. Arg-Arg-Arg-Arg; SEQ ID NO:1) and 28 to 31 (RKVR) (i.e., Arg-Lys-Val-Arg; SEQ ID NO:2) are arginine-rich cationic domains in the N-terminus especially critical to the antimicrobial activities of lactoferrin. A similar region in the N-terminus is found in bovine lactoferrin (residues 17 to 42; FKCRRWQWRMKKLGAP-SITCVRRAFA; i.e., Phe-Lys-Cys-Arg-Arg-Trp-Gln-Trp-Arg-Met-Lys-Lys-Leu-Gly-Ala-Pro-Ser-Ile-Thr-Cys-Val-Arg-Arg-Ala-Phe-Ala; SEQ ID NO:3).

As described in "*Perspectives on Interactions Between Lactoferrin and Bacteria*" which appeared in the publication BIOCHEMISTRY AND CELL BIOLOGY, pp 275-281 (2006), lactoferrins from different host species may vary in their amino acid sequences though commonly possess a relatively high isoelectric point with positively charged amino acids at the end terminal region of the internal lobe. Suitable lactoferrins for use in the present disclosure include those having at least 48% homology with the amino acid sequence AVGEQELRKCN-QWSGL (i.e., Ala-Val-Gly-Glu-Gln-Glu-Leu-Arg-Lys-Cys-Asn-Gln-Trp-Ser-Gly-Leu; SEQ ID NO:4) at the HLf (349-364) fragment. In some embodiments, the lactoferrin has at least 65% homology with the amino acid sequence AVGEQELRKCNQWSGL (i.e., Ala-Val-Gly-Glu-Gln-Glu-Leu-Arg-Lys-Cys-Asn-Gln-Trp-Ser-Gly-Leu: SEQ ID NO:4) at the HLf (349-364) fragment, and, in embodiments, at least 75% homology. For example, non-human lactoferrins acceptable for use in the present disclosure include, without limitation, bovine lactoferrin, porcine lactoferrin, equine lactoferrin, buffalo lactoferrin, goat lactoferrin, murine lactoferrin and camel lactoferrin.

A benefit of lactoferrin, as used in certain embodiments of the present disclosure, is the anti-invasion mechanisms of lactoferrin in the human gut. In particular, lactoferrin inhibits the adhesion of pathogens in the gastrointestinal tract of humans.

One such example of a bacterium known to cause pathogenesis is *Escherichia coli* which may cause diarrhea in infants, children and adults and is realized as an agent for pediatric diarrhea. As defined in "*Lactoferrin Impairs Type III Secretory System Function In Enteropathogenic Escherichia Coli*" as published in INFECTION AND IMMUNITY, pp 5149-5155 (2003), there are generally three stages to enteropathogenic *E. coli* pathogenesis. The first step generally includes adherence to the human cells through a bundle forming pilus.

The secretory system of many gram-negative pathogenic bacteria is a type III secretion including the following bacteria: *Shigella flexneri, Salmonella, Pseudomonas,* and *Escherichia coli.* The type III secretory system functions through use of a needle for the transport of virulent proteins from the bacterial cytoplasm through the needle directly into the host cell's cytoplasm. The use of the needle provides for a passage through the multiple membranes including the double membranes of the gram-negative bacterium and the eukaryotic membrane of the human cell. Specifically, in strains of *E. coli* the needle complex is comprised of *E. coli* secretion component F (EscF) with *E. coli* secreted protein A (EspA) attaching to the tip of the needle, forming a generally hollow structure for the passage of components from the bacteria to the host human cell. At this point, bacterial proteins such as EspB may be introduced into the host cell through this tube. While the physiology of EspB may not be fully understood, in the article "*The Enteropathogenic E. coli effector EspB facilitates microvillus effacing and Antiphagocytosis by Inhibiting Myosin Function*" in CELL HOSTS AND MICROBE, pp 383-392 (2007), EspB is described as binding to myosins which ultimately suppresses phagocytosis as a human immune response. Generally, myosin proteins interact with actin filaments to participate in cellular processes such as phagocytosis in eliminating potential bacterial pathogens. Harmful symptoms occur where EspB emitted by the *E. coli* inhibits the interaction between various myosin proteins and actin filaments in suppressing phagocytosis, leading to diarrhea or other gastric distress in infants, children and adults.

In one embodiment, lactoferrin is present in the nutritional composition in an amount of at least about 10 mg/100 kCal, especially when the nutritional composition is intended for use by children. In certain embodiments, the upper limit for lactoferrin is about 240 mg/100 kCal. In another embodiment, where the nutritional composition is an infant formula, lactoferrin is present in the nutritional composition in an amount of from about 70 mg to about 220 mg/100 kCal; in yet another embodiment, lactoferrin is present in an amount of about 90 mg to about 190 mg/100 kCal. Nutritional compositions for infants can include lactoferrin in the quantities of from about 0.5 mg to about 1.5 mg per milliliter of formula. In nutritional compositions replacing human milk, lactoferrin may be present in quantities of from about 0.6 mg to about 1.3 mg per milliliter of formula.

Preferably, the lactoferrin used in the nutritional compositions retains its stability and activity in the human gut even after processing under conditions of high temperature and low pH. In one embodiment of the present disclosure, the lactoferrin used is non-human lactoferrin.

For example, surprisingly, bovine lactoferrin maintains certain bactericidal activity even if exposed to a low pH (i.e., below 7, and even as low as about 4.6 or lower) and/or high temperatures (i.e., above about 65° C., and as high as about 120° C.), conditions which would be expected to destroy or severely limit the stability or activity of human lactoferrin. These low pH and/or high temperature conditions can be expected during certain processing regimen for nutritional compositions of the types described herein, such as pasteurization. Yet, while bovine lactoferrin has an the amino acid composition which has about a 70% sequence homology to that of human lactoferrin, and is stable and remains active under conditions under which human lactoferrin becomes unstable or inactive, bovine lactoferrin has bactericidal activity against undesirable bacterial pathogens found in the human gut.

In certain embodiments, in addition to lactoferrin, the nutritional compositions comprise a prebiotic composition comprising one or more prebiotics. As used herein, the term "prebiotic" means a non-digestible food ingredient that beneficially affects the host by selectively stimulating the growth and/or activity of one or a limited number of bacteria in the colon that can improve the health of the host. A "prebiotic composition" is a composition that comprises one or more prebiotics. Such prebiotics may be naturally-occurring, synthetic, or developed through the genetic manipulation of organisms and/or plants, whether such new source is now known or developed later. In certain embodiments, the prebiotic included in the compositions of the present disclosure include those taught by U.S. Pat. No. 7,572,474, the disclosure of which is incorporated herein by reference.

Prebiotics useful in the present disclosure may include oligosaccharides, polysaccharides, and other prebiotics that contain fructose, xylose, soya, galactose, glucose and mannose. More specifically, prebiotics useful in the present disclosure may include lactulose, lactosucrose, raffinose, gluco-oligosaccharide, inulin, polydextrose, polydextrose powder, galactooligosaccharide, fructo-oligosaccharide, isomalto-oligosaccharide, soybean oligosaccharides, lactosucrose, xylo-oligosacchairde, chito-oligosaccharide, manno-oligosaccharide, aribino-oligosaccharide, siallyl-oligosaccharide, fuco-oligosaccharide, and gentio-oligosaccharides. Preferably, the nutritional compositions comprise polydextrose and/or galactooligosaccaharide. Optionally, in addition to polydextrose and/or galactooligosaccaharide, the nutritional compositions comprise one or more additional prebiotics.

In an embodiment, the total amount of prebiotics present in the nutritional composition may be from about 0.1 g/100 kcal to about 1 g/100 kcal. More preferably, the total amount of prebiotics present in the nutritional composition may be from about 0.3 g/100 kcal to about 0.7 g/100 kcal. At least 20% of the prebiotics should comprise galactooligosaccharide (GOS) and/or polydextrose (PDX).

If polydextrose is used in the prebiotic composition, the amount of polydextrose in the nutritional composition may, in an embodiment, be within the range of from about 0.1 g/100 kcal to about 1 g/100 kcal. In another embodiment, the amount of polydextrose is within the range of from about 0.2 g/100 kcal to about 0.6 g/100 kcal.

If galactooligosaccharide is used in the prebiotic composition, the amount of galactooligosaccharide in the nutritional composition may, in an embodiment, be from about 0.1 g/100 kcal to about 1 g/100 kcal. In another embodiment, the amount of galactooligosaccharide in the nutritional composition may be from about 0.2 g/100 kcal to about 0.5 g/100 kcal. In certain embodiments, the ratio of polydextrose to galactooligosaccharide in the prebiotic composition is between about 9:1 and about 1:9.

Preferably, the prebiotic composition, in combination with lactoferrin, inhibits the adhesion of one or more pathogens in the gastrointestinal tract when the nutritional compositions are provided to humans. An example of one such pathogen is *Enterobacter sakazakii* (otherwise known as *Cronobacter sakazakii*). Preferably, the nutritional compositions are provided to an infant or a child. As used herein, the term "infant" is generally defined as a human from birth to 12 months of age. A "child" and "children" are defined as humans over the age of 12 months to about 12 years old.

In some embodiments, the nutritional composition may be an infant formula. The term "infant formula" applies to a composition in liquid or powdered form that satisfies the nutrient requirements of an infant by being a substitute for human milk. In the United States, the content of an infant formula is dictated by the federal regulations set forth at 21 C.F.R. §§100, 106 and 107. These regulations define macronutrient, vitamin, mineral, and other ingredient levels in an effort to simulate the nutritional and other properties of human breast milk. In a separate embodiment, the nutritional product may be a human milk fortifier, meaning it is a composition which is added to human milk in order to enhance the nutritional value of human milk. As a human milk fortifier, the disclosed composition may be in powder or liquid form. In yet another embodiment, the disclosed nutritional product may be a children's nutritional composition.

The nutritional compositions of the disclosure may provide minimal, partial, or total nutritional support. The nutritional compositions may be nutritional supplements or meal replacements. In some embodiments, the nutritional compositions may be administered in conjunction with a food or another nutritional composition. In this embodiment, the nutritional compositions can either be intermixed with the food or other nutritional composition prior to ingestion by the subject or can be administered to the subject either before or after ingestion of a food or nutritional composition. The nutritional compositions may be administered to preterm infants receiving infant formula, breast milk, a human milk fortifier, or combinations thereof. For purposes of the present disclosure, a "preterm infant" is an infant born after less than 37 weeks gestation, while a "full term infant" is an infant born after at least 37 weeks gestation.

The nutritional compositions may, but need not, be nutritionally complete. The skilled artisan will recognize "nutritionally complete" to vary depending on a number of factors including, but not limited to, age, clinical condition, and dietary intake of the subject to whom the term is being applied. In general, "nutritionally complete" means that the nutritional composition of the present disclosure provides adequate amounts of all carbohydrates, lipids, essential fatty acids, proteins, essential amino acids, conditionally essential amino acids, vitamins, minerals, and energy required for normal growth. As applied to nutrients, the term "essential" refers to any nutrient which cannot be synthesized by the body in amounts sufficient for normal growth and to maintain health and which therefore must be supplied by the diet. The term "conditionally essential" as applied to nutrients means that the nutrient must be supplied by the diet under conditions when adequate amounts of the precursor compound is unavailable to the body for endogenous synthesis to occur.

The composition which is "nutritionally complete" for the preterm infant will, by definition, provide qualitatively and quantitatively adequate amounts of all carbohydrates, lipids, essential fatty acids, proteins, essential amino acids, conditionally essential amino acids, vitamins, minerals, and energy required for growth of the preterm infant. The composition which is "nutritionally complete" for the full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant. The composition which is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

The nutritional composition may be provided in any form known in the art, including a powder, a gel, a suspension, a paste, a solid, a liquid, a liquid concentrate, or a ready-to-use product. In one preferred embodiment, the nutritional composition is an infant formula, especially an infant formula adapted for use as sole source nutrition for an infant.

In the preferred embodiments, the nutritional product disclosed herein may be administered enterally. As used herein, "enteral" means through or within the gastrointestinal, or digestive, tract, and "enteral administration" includes oral feeding, intragastric feeding, transpyloric administration, or any other introduction into the digestive tract.

Suitable fat or lipid sources for practicing the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palmolein, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

In certain embodiments, the protein source included in the nutritional composition comprises bovine milk proteins. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In one embodiment, the proteins are provided as intact proteins. In other embodiments, the proteins are provided as a combination of both intact proteins and partially hydrolyzed proteins, with a degree of hydrolysis of between about 4% and 10%. In yet another embodiment, the protein source may be supplemented with glutamine-containing peptides.

In a particular embodiment of the disclosure, the protein source comprises whey and casein proteins and the ratio of whey to casein proteins ratio is similar to that found in human breast milk. For example, in certain embodiments, the weight ratio of whey to casein proteins is from about 20% whey:80% casein to about 80% whey:20% casein.

In one embodiment of the disclosure, the nutritional composition may contain one or more probiotics. The term "probiotic" means a microorganism with low or no pathogenicity that exerts beneficial effects on the health of the host. Any probiotic known in the art may be acceptable in this embodiment provided it achieves the intended result. In a particular embodiment, the probiotic may be selected from *Lactobacillus* species, *Lactobacillus rhamnosus* GG, *Bifidobacterium* species, *Bifidobacterium brevis, Bifidobacterium longum*, and *Bifidobacterium animalis* subsp. *lactis* BB-12.

If included in the composition, the amount of the probiotic may vary from about $10^4$ to about $10^{10}$ colony forming units (cfu) per kg body weight per day. In another embodiment, the amount of the probiotic may vary from about $10^6$ to about $10^9$ cfu per kg body weight per day. In yet another embodiment, the amount of the probiotic may be at least about $10^6$ cfu per kg body weight per day.

In an embodiment, one or more of the probiotic(s) is viable. In another embodiment, one or more of the probiotic(s) is non-viable. As used herein, the term "viable" refers to live microorganisms. The term "non-viable" or "non-viable probiotic" means non-living probiotic microorganisms, their cellular components and metabolites thereof. Such non-viable probiotics may have been heat-killed or otherwise inactivated but retain the ability to favorably influence the health of the host. The probiotics useful in the present disclosure may be naturally-occurring, synthetic or developed through the genetic manipulation of organisms, whether such new source is now known or later developed.

The nutritional formulation of the disclosure, in some embodiments, may further contain a source of long chain polyunsaturated fatty acids (LCPUFAs). Preferably, the source of LCPUFAs comprise docosahexanoic acid (DHA). Other suitable LCPUFAs include, but are not limited to, α-linoleic acid, γ-linoleic acid, linoleic acid, linolenic acid, eicosapentanoic acid (EPA) and arachidonic acid (ARA).

In one embodiment, the nutritional composition is supplemented with both DHA and ARA. In this embodiment, the weight ratio of ARA:DHA may be from about 1:3 to about 9:1. In one embodiment of the present disclosure, the weight ratio of ARA:DHA is from about 1:2 to about 4:1.

The amount of long chain polyunsaturated fatty acids in the nutritional composition may vary from about 5 mg/100 kcal to about 100 mg/100 kcal, more preferably from about 10 mg/100 kcal to about 50 mg/100 kcal.

The nutritional composition may be supplemented with oils containing DHA and ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If utilized, the source of DHA and ARA may be any source known in the art such as marine oil, fish oil, single cell oil, egg yolk lipid, and brain lipid. In some embodiments, the DHA and ARA are sourced from the single cell Martek oil, DHASCO® and ARASCO® respectively, or variations thereof. The DHA and ARA can be in natural form, provided that the remainder of the LCPUFA source does not result in any substantial deleterious effect on the infant. Alternatively, the DHA and ARA can be used in refined form.

In an embodiment of the present disclosure, sources of DHA and ARA are single cell oils as taught in U.S. Pat. Nos. 5,374,567; 5,550,156; and 5,397,591, the disclosures of which are incorporated herein in their entirety by reference. However, the present disclosure is not limited to only such oils.

In certain embodiments, the nutritional compositions comprise from about 0.5 mg/100 kcal to about 5 mg/100 kcal of iron, including iron bound to lactoferrin.

EXAMPLES

The following examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

Example 1

This Example exemplifies the inhibition of pathogens, namely *E. sakazakii* 4603 and 29004 and *E. coli* E2348169, by lactoferrin alone and in combination with polydextrose and galactooligosaccharide.

Based on a preliminary experiment, it is determined that cultures of *E. sakazakii* 4603 and 29004 give the highest adherence rates to HEp-2 cells. After 6 hour incubation, cultures of these *E. sakazakii* strains as well as cultures of *E. coli* E2348169 are harvested by centrifugation, washed with phosphate buffered saline, and re-suspended in minimal essential medium (MEM) supplemented with 10% fetal bovine serum. HEp-2 cells (obtained from the ATTC) are grown in 75 cm$^2$ tissue culture flasks containing 25 ml of MEM supplemented with 10% FBS in a $CO_2$ incubator at tissue culture conditions. Confluent HEp-2 cells are harvested by adding 0.5 ml of 0.25% Trypsin-EDTA Solution (Sigma) and incubating for 15 minutes at tissue culture conditions. Trypsin is inactivated with 0.5 ml of FBS, and the cells are seeded onto 12-mm diameter glass coverslips in 24-well tissue culture plates at approximately 3.6×10$^5$ viable cells per well. Plates are incubated under tissue culture conditions for two days prior to the start of each experiment, or until confluency is reached.

Immediately before the start of the assay, lactoferrin at final concentrations of 0.1 mg/ml, 0.6 mg/ml, and 1 mg/ml, alone and in combination with a 1:1 blend of galactooligosaccharide (obtained from DOMO) and polydextrose (obtained from DMV) at final concentrations of 4 mg/ml and 16 mg/ml of, is added to the HEp-2 cells. Control wells containing no lactoferrin are also prepared. Then, 900:1 of the *E. coli* or *E. sakazakii* culture (containing ca. 10$^7$ cells) are added to each well (in triplicate). Tissue culture plates are then incubated at 37° C. in a $CO_2$ incubator for three hours. The wells are then washed five times to remove non-adherent cells, and adhered bacteria are enumerated by microscopic enumeration and quantitative real-time PCR.

For microscopic enumeration, coverslips are fixed with 100% methanol, stained with 10% Geimsa for 15 minutes, washed with distilled water, and dried overnight. The coverslips are mounted on microscope slides and observed under a phase contrast microscope with the 100× objective. Fifteen photomicrographs of each coverslip are taken using Motic Image software following an established geometric pattern throughout the entire coverslip. The number of cells and bacteria in each image is counted using Image J image analysis software. Adherence is calculated as the number of adhered bacteria per HEp-2 cell. Adherence inhibition is calculated as the number of adhered bacteria per cell in the control minus the number of adhered bacteria per cell in the treatment divided by the number of adhered bacteria per cell in the control. For experiments using cultures of *E. coli*, cells with *E. coli* microcolonies are manually counted. Cells with four or more bacteria are considered positive for having a typical localized adherence phenotype. The number of HEp-2 cells with adhered microcolonies is determined and adherence and adherence inhibition is calculated as described above. Experiments are performed in triplicate and replicated three times (n=9).

In addition to the microscopic enumeration, adhered cells are also enumerated by quantitative real-time PCR (qRT-PCR), as described in Humphries et al., Interactions of enteropathogenic *Escherichia coli* with pediatric and adult intestinal biopsy specimens during early adherence, Infect. Immun., 77, 4463-4468 (2009). Briefly, genomic DNA are extracted from the infected HEp-2 cells and quantified by qRT-PCR using oligonucleotide primers that amplify the 16s rRNA region of *E sakazakii* 4603 and 29004 or *E. coli* 2348/69. Appropriately diluted whole genomic DNA is used as internal controls and to prepare standard curves relating qPCR endpoints to cell concentrations. The PCR mixture consists of 11.25 µl SYBR solution, 2.5 MasterMix, 1 µl of each primer, and 5 µl of DNA template. The PCR reactions are performed using an Eppendorf Mastercycler Realplex2.

Example 2

This example illustrates an embodiment of a nutritional product according to the present disclosure.

| Description | kg per 100 kg |
|---|---|
| carbohydrate, total | 38.9 |
| protein, total | 28.8 |
| fat, total | 25.6 |
| prebiotics | 4.5 |
| soy lecithin | 0.8 |
| lactoferrin | 0.3 |
| calcium carbonate | 0.5 |
| potassium citrate | 0.2 |
| ferrous sulfate | 0.05 |
| potassium chloride | 0.048 |
| magnesium oxide | 0.023 |
| sodium chloride | 0.025 |
| zinc sulfate | 0.015 |
| cupric sulfate | 0.002 |
| manganese sulfate | 0.0003 |
| sodium selenite | 0.00003 |
| choline chloride | 0.144 |
| ascorbic acid | 0.093 |
| Niacinamide | 0.006 |
| calcium pantothenate | 0.003 |
| vitamin A palmitate | 0.007 |
| vitamin B12 | 0.002 |
| vitamin D3 | 0.000001 |
| Riboflavin | 0.0008 |
| thiamin | 0.0006 |
| vitamin B6 | 0.0004 |
| folic acid | 0.0001 |
| vitamin K1 | 0.006 |
| biotin | 0.00002 |
| inositol | 0.03 |
| vitamin E acetate | 0.01 |
| taurine | 0.05 |
| L-carnitine | 0.001 |

Example 3

This example illustrates another embodiment of a nutritional product according to the present disclosure.

| Description | kg per 100 kg |
|---|---|
| carbohydrate, total | 24.7 |
| protein, total | 31.9 |
| fat, total | 39.3 |
| prebiotics | 3.6 |
| lactoferrin | 0.1 |
| calcium carbonate | 0.15 |
| ferrous sulfate | 0.03 |
| zinc sulfate | 0.01 |
| copper sulfate | 0.00025 |
| manganese sulfate | 0.0002 |

-continued

| Description | kg per 100 kg |
|---|---|
| sodium selenite | 0.00001 |
| choline bitartrate | 0.05 |
| ascorbic acid | 0.004 |
| sodium ascorbate | 0.04 |
| niacinamide | 0.007 |
| calcium pantothenate | 0.0005 |
| vitamin A palmitate | 0.0005 |
| vitamin D3 | 0.0002 |
| riboflavin | 0.0001 |
| thiamin | 0.00005 |
| vitamin B6 | 0.00005 |
| folic acid | 0.000067 |
| vitamin K1 | 0.00002 |
| vitamin E acetate | 0.008 |
| taurine | 0.02 |
| fish oil | 0.2 |
| B-glucan | 0.03 |

Example 4

This example illustrates one embodiment of ingredients that can be used to prepare the nutritional product according to the present disclosure.

| | |
|---|---|
| water | 872 ml |
| lactose | 65.6 mg |
| vegetable oil blend | 353.0 mg |
| nonfat milk evaporated | 34.0 mg |
| whey protein concentrate | 8.5 mg |
| galacto-oligosaccharide | 4.7 mg |
| casein | 3.5 mg |
| polydextrose | 2.4 mg |
| lactoferrin solution (10%) | 1.0 mg |
| single cell DHA and ARA oil blend | 0.94 mg |
| mono- and di-glycerides | 0.7 mg |
| calcium carbonate | 0.44 mg |
| calcium phosphate | 0.4 mg |
| potassium citrate | 0.4 mg |
| potassium chloride | 0.4 mg |
| soy lecithin | 0.4 mg |
| sodium chloride | 0.3 mg |
| potassium phosphate | 0.3 mg |
| choline chloride | 0.2 mg |
| magnesium oxide | 0.08 mg |
| calcium hydroxide | 0.08 mg |
| ferrous suflate | 0.07 mg |

Example 5

This example illustrates another embodiment of ingredients that can be used to prepare the nutritional product according to the present disclosure.

| | |
|---|---|
| water | 686 ml |
| reduced minerals whey | 215 mg |
| nonfat milk evaporated | 67 mg |
| vegetable oil blend | 33 mg |
| lactose | 17 mg |
| galacto-oligosaccharide | 4.7 mg |
| polydextrose | 2.4 mg |
| lactoferrin solution (10%) | 1.0 mg |
| single cell DHA and ARA oil blend | 0.9 mg |
| mono- and di-glycerides | 0.7 mg |
| calcium carbonate | 0.44 mg |
| calcium phosphate | 0.4 mg |
| potassium citrate | 0.4 mg |
| potassium chloride | 0.4 mg |
| soy lecithin | 0.4 mg |
| potassium phosphate | 0.3 mg |
| carrageenan | 0.3 mg |
| sodium citrate | 0.2 mg |
| choline chloride | 0.2 mg |
| magnesium oxide | 0.08 mg |
| calcium chloride | 0.08 mg |
| ferrous suflate | 0.07 mg |

Preferably, the nutritional composition is administered to a human and inhibits the adhesion of at least one pathogen in the gastrointestinal tract of the human.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although preferred embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged both in whole or in part. For example, while methods for the production of a commercially sterile liquid nutritional supplement made according to those methods have been exemplified, other uses are contemplated. Therefore, the spirit and scope of the appended claims should not be limited to the description of the preferred versions contained therein.

What is claimed is:

1. A method for inhibiting the adhesion of at *Cronobacter sakazakii* in the gastrointestinal tract of a human, comprising administering to the human a nutritional composition comprising:
   a) a fat or lipid source;
   b) a non-lactoferrin protein source;
   c) at least about 10 mg/100 kcal of lactoferrin produced by a non-human source; and
   d) about 0.1 g/100 kcal to about 1 g/100 kcal of a prebiotic composition comprising a compound selected from a galactooligosaccharide, polydextrose, and a combination thereof.

2. The method according to claim 1, wherein the human is an infant or a child.

3. The method according to claim 1, wherein the fat or lipid source is present at a level of about 3 g/100 kcal to about 7 g/100 kcal.

4. The method according to claim 1, wherein the non-lactoferrin protein source is present at a level of about 1 g/100 kcal to about 5 g/100 kcal.

5. The method according to claim 1, wherein the lactoferrin is present at a level of about 70 mg/100 kcal to about 220 mg/100 kcal.

6. The method according to claim 1, wherein the lactoferrin is selected from the group consisting of non-human lactoferrin, human lactoferrin produced by a genetically modified organism, and a combination thereof.

7. The method according to claim 1, wherein the lactoferrin is stable and remains active under conditions under which human lactoferrin becomes unstable or inactive.

8. The method according to claim 7, wherein the nutritional composition has been subject to pasteurization conditions.

9. The method according to claim 1, wherein the prebiotic composition comprises a galactooligosaccharide.

10. The method according to claim 9, wherein the prebiotic composition further comprises polydextrose.

11. The method according to claim 10, wherein the ratio of polydextrose to galactooligosaccharide is between about 9:1 and about 1:9.

12. The method according to claim 1, further comprising the step of administering at least one probiotic.

13. The method according to claim 12, wherein the probiotic is selected from the group consisting of *Bifidobacteria* spp., *Lactobacillus* spp. and combinations thereof.

14. The method according to claim 1, wherein the nutritional composition comprises about 0.5 mg/100 kcal to about 5 mg/100 kcal of iron, including iron bound to lactoferrin.

15. The method according to claim 1, wherein the nutritional composition further comprises about 5 mg/100 kcal to about 100 mg/100 kcal of at least one source of long chain polyunsaturated fatty acids.

16. The method according to claim 15, wherein the source of long chain polyunsaturated fatty acids is selected from the group consisting of docosahexaenoic acid, arachidonic acid, and a combination thereof.

17. The method according to claim 16, wherein the source of long chain polyunsaturated fatty acids is docosahexaenoic acid and arachidonic acid.

18. The method according to claim 17, wherein the ratio of arachidonic acid to docosahexaenoic acid is from about 1:3 to about 9:1.

* * * * *